US00PP12500P2

(12) United States Plant Patent
Zerr

(10) Patent No.: US PP12,500 P2
(45) Date of Patent: Apr. 2, 2002

(54) POINSETTIA PLANT NAMED 'FISSON ORANGE'

(75) Inventor: Katharina Zerr, Simmern (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/210,121

(22) Filed: Dec. 11, 1998

(51) Int. Cl.[7] ..... A01H 5/00
(52) U.S. Cl. ..... Plt./307
(58) Field of Search ..... Plt./307, 303

(56) References Cited

PUBLICATIONS

UPOV–ROM GTITM Computer Database 1999/02, GTI JOUVE Retrieval Software, citations for 'Fission Orange', May 1999.*

German Application—FISMILLE—Dec. 15, 1997.

German Denomination—FISMILLE—Aug. 15, 1998.

Canadian Application—FISMILLE—Aug. 18, 1997.

Fischer Poinsettia Catalogue—Germany (1998), p. 16 (FISMILLE).

* cited by examiner

*Primary Examiner*—Bruce R. Campell
*Assistant Examiner*—Michelle Kizilkaya
(74) *Attorney, Agent, or Firm*—Foley & Lardner

(57) ABSTRACT

'Fisson Orange' is characterized by uniform orange-red bract color of medium size; flat involucre with strongly lobed bracts; intense dark-green foliage with distinct lobes; compact and very well-branched, round plant habit; and medium to early flowering response.

1 Drawing Sheet

BACKGROUND OF THE INVENTION

The present invention relates to a new and distinct cultivar of Poinsettia plant known by the cultivar name 'Fisson Orange' and botanically known as *Euphorbia pulcherrima.*

'Fisson Orange' is a product of a mutation induction program carried out by the inventor, Katharina Zerr, in Hillscheid, Germany, in 1994. The primary objective of the induction program was to expand the bract color ranges of 'Fisson' (U.S. Plant Pat. No. 9,365). 'Fisson' is characterized by its intense red-colored bracts with pointed lobes, dark-green foliage and relatively compact habit.

The irradiation program comprised exposing rooted cuttings taken from plants of the parent cultivar to an X-ray source of 30 Gy dosage in Ahrensburg, Germany, under the supervision of the inventor. The irradiated plants were grown out in a greenhouse and were asexually propagated, in Hillscheid, Germany, by the inventor by taking cuttings. The plants resulting from these cuttings were screened for mutations as small flowering, single-stem plants beginning in autumn of 1994 and continuing thereafter. The mutations discovered were identified by numbers. Parts of plants exhibiting a mutation of interest were left to develop vegetative shoots which were used as cuttings and grown out.

'Fisson Orange' originated from a single plant (no. 550) which exhibited more orange-red colored bracts and was discovered in the late summer of 1995. The selection was propagated vegetatively by cuttings and the cuttings were screened for uniformity in the spring of 1996 prior to further propagation. The clone was examined more closely in the autumn of 1996 and again in the late summer of 1997. Horticultural examination of the clone starting in 1997 and continuing thereafter has confirmed that the combination of characteristics as herein disclosed for 'Fisson Orange' are firmly fixed and retained through successive generations of asexual reproduction.

BRIEF DESCRIPTION OF THE INVENTION

The following traits have been repeatedly observed and are determined to be basic characteristics of 'Fisson Orange' which in combination distinguish this Poinsettia as a new and distinct cultivar:

1. Uniform orange-red bract color of medium size;
2. Flat involucre with strongly lobed bracts;
3. Intense dark-green foliage with distinct lobes;
4. Compact and very well-branched, round plant habit; and
5. Medium to early flowering response.

'Fisson Orange' has not been observed under all possible environmental conditions. The phenotype may vary significantly with variations in environment such as temperature, light intensity, and daylength without a change in genotype. The following observations, measurements and comparisons describe plants grown in Langley, British Columbia, Canada, under greenhouse conditions which approximate those generally used in commercial practice.

Of the many commercial cultivars known to the inventor, the most similar in comparison to 'Fisson Orange' is the parent cultivar 'Fisson'. In comparison to 'Fisson', 'Fisson Orange' has more orange-red colored bracts with an even better stability under summer conditions, without tendency to fade or develop a bluish hue. 'Fisson Orange' appears to produce even more branches, which results in slightly more numerous and, therefore, somewhat smaller and stronger-lobed inflorescence. Furthermore, the reddish anthocyanin coloring of stems and petioles is not quite as intense as with 'Fisson'. Compared to the sibling cultivar 'Fiscor Hot Pink' (U.S. Plant patent application Ser. No. 09/209,754), 'Fisson Orange' has significantly different coloration of both the petiole and upper bract surface.

BRIEF DESCRIPTION OF THE DRAWING

The accompanying color photographic sheet shows typical inflorescence and foliage of a mature potted plant of 'Fisson Orange', with colors being as true as possible with illustrations of this type.

DETAILED BOTANICAL DESCRIPTION

The plants described were grown in a greenhouse in Langley, British Columbia, Canada, in autumn of 1997. Rooted cuttings were planted into 15-cm pots on August 1, and were pinched on August 18, leaving 8 nodes. The minimum temperature was 23° C. until October 10, 20° C. to mid-November, and lower thereafter. The plants initiated flowers under natural short-day conditions in autumn.

Observations and measurements were mainly taken at the beginning of flowering. In the following description, color references are made to The Royal Horticultural Society Colour Chart (R.H.S.). The color values were determined indoors in a north light.

Classification:

*Botanical.*—*Euphorbia pulcherrima.*

*Commercial.*—Poinsettia, cv. 'Fisson Orange'.

Parentage: Induced mutation of 'Fisson'.

Plant:

*Form.*—Shrub, self-branching.

*Growth habit.*—Relatively compact, weak to medium growth, pinched plants are bushy and round in shape. Height, including pot, is 41 cm. The average number of branches is 9.6.

*Stem color.*—Relatively light-green, R.H.S. 143 A to B, with very weak infusion of anthocyanin.

*Rooting.*—Medium, about 20–24 days.

*Blooming habit.*—Flowering response time under natural short-day conditions in autumn: botanically, cyathia open, around December 1; commercially, bracts colored and marketable, in late November.

*Flowering response time.*—About 9 weeks.

*Keeping quality.*—For approximately 4 weeks or more, plants show no tendency towards fading or drooping and good retention of foliage and bracts.

Foliage:

*Shape.*—Basal part roughly triangular, acute base, acuminated tip, and most often with strong, pointed lobes; smaller leaves without lobes are broad elliptically shaped.

*Margin.*—Entire.

*Texture.*—Upper surface: Smooth and flat, only weakly veined; color of veins is R.H.S. 146 D or lighter, with the basal part of midrib having reddish coloring like the petiole. Lower surface: Flat and smooth, except for the slightly protruding midrib and finer side veins, which protrude at an acute, almost right-angle from the midrib; the herringbone side veins are evenly spread throughout the leaf pattern blade and run parallel to each other; the vein color is a very light-green, R.H.S. 145 C.

*Size.*—Leaf blade length is 12.0 cm; leaf blade width is 8.0 cm; petiole length is 5.8 cm.

*Color.*—Generally a uniform dark-green. Mature foliage: Upper surface is R.H.S. 139 A; under surface is R.H.S. 137 B. New foliage: Upper side is about R.H.S. 143 A; under side is about R.H.S. 137 D.

*Petiole color.*—Brownish-red, near R.H.S. 181 A.

*Aspect.*—Petioles are horizontally directed, while the leaf blades show slightly downward.

*Disease resistance.*—Typical, no special observations made.

Flowering description:

*Inflorescence.*—Flat and horizontally directed or slightly downward. The diameter of inflorescence is about 25 cm.

*Number of inflorescences per plant.*—Approximately 8.9.

*Number of bracts per inflorescence.*—9–10 true bracts, each over 2 cm in length.

*Size of bract.*—The length is 12.5 cm and width is 9.7 cm; petiole is 1.8 cm.

*Bracts, shape.*—The basal part of the larger bracts is roughly triangular, with acute base, distinctly lobed with pointed tips, and with acuminated tip; the smaller, younger bracts are broad elliptically shaped and usually without lobes.

*Texture.*—Flat, or slightly folded along the midrib, smooth at the beginning of flowering, with veins hardly visible, as bracts mature, veins may create a somewhat rugose pattern, the veins are arranged in a herringbone pattern, the vein color of the upper side corresponds to the bract color or appears slightly darker, while the veins on the underside are usually lighter brownish-pink, R.H.S. 47A–B or lighter.

*Color.*—Generally an intense scarlet-red, uniform, without tendency to fading near the margin. Upper surface: R.H.S. 44 A to 45 B. Lower surface: R.H.S. 45 D.

*Petiole, color.*—Red, between R.H.S. 46 A and B.

*Cyathia.*—Few, about 10 in a narrow cluster, about 20 mm wide; diameter of the single cyathium is 5–6 mm.

*Color.*—Mainly light-green, R.H.S. 143 C, with darker, medium-green patches, about R.H.S. 137 D; top is red, about R.H.S. 45 B.

*Retention.*—Medium in comparison to other varieties.

*Nectar cups.*—Small to medium-sized, bright yellow, usually no anthocyanin coloring near margin.

Reproductive organs:

*Stamens.*—Red filaments, fertile, yellow pollen.

*Pistils.*—Style and stigma are red; 6-lobed stigma.

*Ovaries.*—Triangular, 3 ovules.

*Fruit seed set.*—Spontaneous seed set was seldom observed under common winter conditions but was fertile when pollinated.

I claim:

1. A new and distinct poinsettia plant named 'Fisson Orange', substantially as illustrated and described.

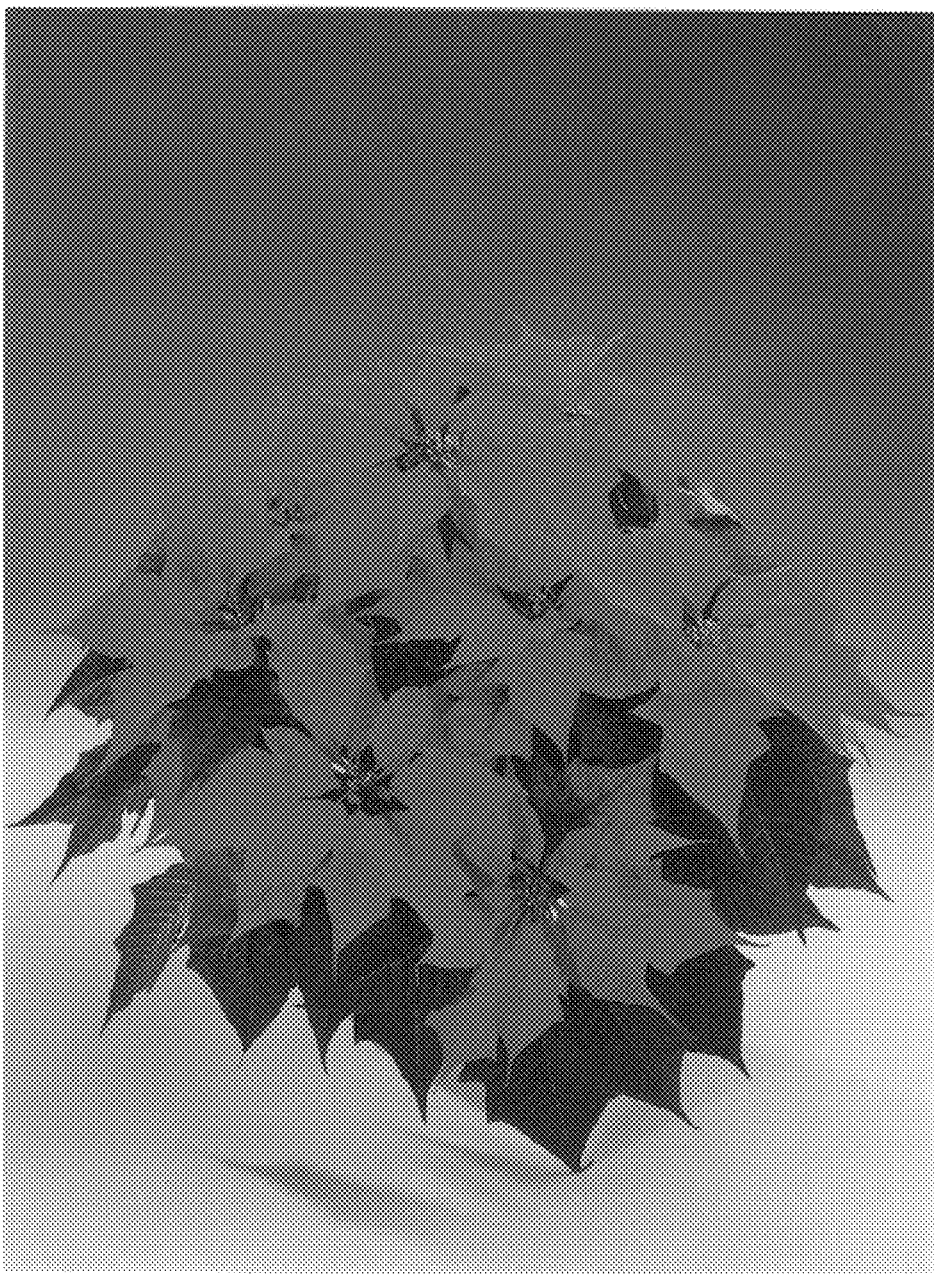

* * * * *